United States Patent [19]

Sheldon

[11] Patent Number: 4,733,802

[45] Date of Patent: Mar. 29, 1988

[54] EYE DROP DISPENSING SYSTEM

[76] Inventor: Gerald M. Sheldon, 11538 S. Lou-Al Ct., Houston, Tex. 77024

[21] Appl. No.: 927,324

[22] Filed: Nov. 5, 1986

[51] Int. Cl.4 ............................................. B67D 5/06
[52] U.S. Cl. .................... 222/181; 604/302
[58] Field of Search ........................... 222/180–181, 222/185, 192, 420; 604/289, 294, 300, 301, 302

[56] References Cited

U.S. PATENT DOCUMENTS

| D. 244,670 | 6/1977 | Winikoff | D9/261 |
|---|---|---|---|
| 1,767,080 | 6/1930 | King | 604/301 |
| 2,898,911 | 8/1959 | Taylor | 604/301 |
| 2,920,624 | 1/1960 | Lerner et al. | 604/301 |
| 3,016,898 | 1/1962 | Erwin | 604/301 |
| 3,058,466 | 10/1962 | Routsong | 604/302 |
| 3,279,466 | 10/1966 | Mings | 604/302 |
| 3,934,590 | 1/1976 | Campagna et al. | 604/302 |
| 4,085,750 | 4/1978 | Bosshold | 604/302 |
| 4,111,200 | 9/1978 | Sbarra et al. | 128/233 |
| 4,158,361 | 6/1979 | Kotuby | 604/302 |

OTHER PUBLICATIONS

"Methods for Self Administration of Eyedrops"; Annals of Ophthalmology, vol. 17, No. 12, Dec. 1985, pp. 768–769.

*Primary Examiner*—Michael S. Huppert
*Attorney, Agent, or Firm*—Ben D. Tobor

[57] ABSTRACT

An eye drop dispensing system for dispensing eye drops upon an eye of an eye drop user includes a single opening formed in a sloping wall surface of an eye drop bottle support, wherein the patient may insert his finger through the opening to retract his or her lower eyelid and to maintain the lower eyelid in its open position while an eye drop is being dispensed.

10 Claims, 3 Drawing Figures

U.S. Patent    Mar. 29, 1988    4,733,802
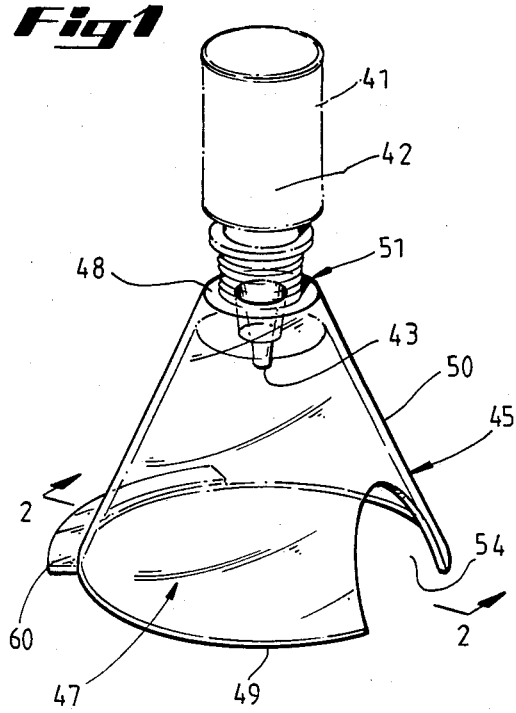
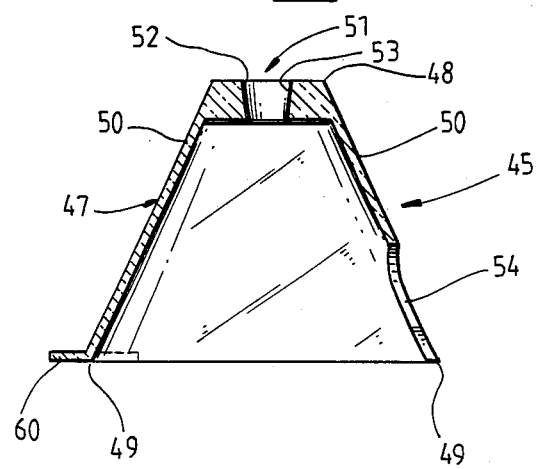
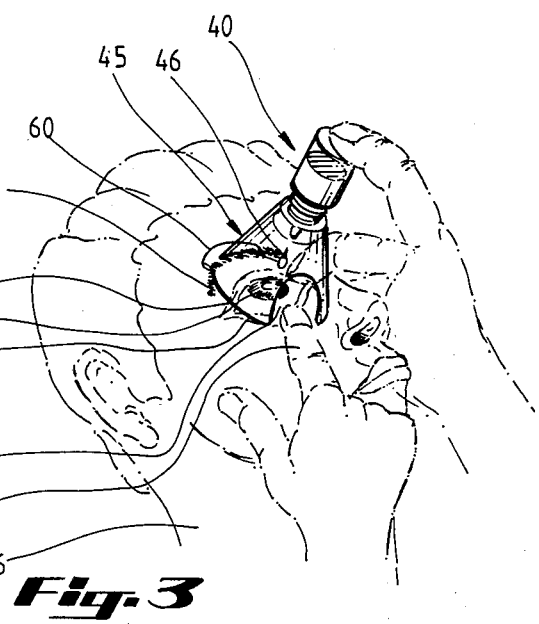

EYE DROP DISPENSING SYSTEM

FIELD OF THE INVENTION

The invention relates to an eye drop dispensing system for dispensing eye drops upon an eye, and in particular an eye drop bottle support.

DESCRIPTION OF THE PRIOR ART

Liquid medications and cleansing fluids for the eye are commonly available in eye drop bottles, which are typically of the squeeze type and made of a suitable, flexible plastic material. These eye drop bottles typically include a small nozzle through which the drops may be dispensed to fall upon the eye drop user's eye. As is well known in the art, such eye drop bottles have many disadvantages and problems associated therewith.

One of the major problems associated with the present eye drop bottles for eye drop instillation is that the eye drops frequently are dispensed upon the eyelids, rather than upon the eye. The causes of such misplacement may be due to: the eye drop user's, poor hand control due to arthritis, or other medical conditions such as Parkison's Disease; or the eye drop user's inability to overcome his or her involuntary eye lid-blink reflex, which causes the eye drop user to blink prior to the eye drop being dispensed upon the eye. With respect to liquid medications being dispensed upon the eye for treatment of an eye condition, a physician monitoring the treatment of the eye condition of the eye drop user, or patient, is uncertain whether of not the condition being treated is not improving because the medication is inadequate, or the medication is not being properly dispensed upon the eye. If the medication is not being properly dispensed, rather than a problem associated with the medication, doubling the dosage of the liquid medication would have no effect upon the eye condition. Furthermore, it is believed that when patients have difficulty instilling, or placing, drops in their eye, the patient will frequently not use the medication properly and the treatment will be ineffective. Additional problems and disadvantages associated with present eye drop bottles are that the patient may touch his eyelids with the eye drop bottle, which can thus cause bacterial contamination of the liquid medication contained in the eye drop bottle. Another disadvantage is that were a patient to apply improper pressure to the upper eyelid, or if the eye drop bottle itself presses against the eye, stress can be caused upon a post-operative eye, which typically has had various incisions made therein. Such contact and/or pressure causes a risk of the potential rupturing, or opening, of the incision.

Furthermore, many patients who realize they are not properly instilling, or placing, the eye drops upon their eye, are believed to overcompensate for their inability to properly administer the eye drops. Thus, such patients will attempt to dispense an excessive number of eye drops, with a view to place enough eye drops on the outside of the eyelid, which they hope will be washed into the eye upon their subsequently opening the eyelid and/or blinking their eyes repeatedly. Since some liquid medications for the eye are extremely potent, it is imperative that the correct dosage be applied to the eye. Examples of such medications include beta blockers which can cause systemic side-effects, and potentially death, if such medication is applied in an overdose fashion.

Numerous eye drop dispenser attachments and systems have been proposed over the years to attempt to solve the foregoing described problems and disadvantages; however, in general, such devices have not met with much success in solving the foregoing described problems and disadvantages. Typically, such prior art eye drop dispenser attachments and systems have required an excessive amount of eye-hand coordination in order to be used and/or required the use of additional devices, such as mirrors for their use. Further, some of these prior art devices included various types of elongate leg members which could readily be inadvertently placed upon the eyelid or eye or the patient, thus damaging the patient's eye. In general, such prior art eye drop dispenser devices merely serve as a support for the eye drop bottle rather than assist the eye drop user in overcoming his or her involuntary eyelid-blink reflex.

Accordingly, prior to the development of the present invention, there has been no eye drop dispensing system for dispensing eye drops upon an eye of an eye drop user, which: may be readily used by eye drop users who have poor vision and/or poor hand control; prevents contact by the eye drop bottle to the eye; prevents improper pressure being applied to the eye and/or upper eyelid; promotes the instillation of the correct number of eye drops upon the patient's eye; and which is simple and economical to manufacture and use.

Therefore, the art has sought an eye drop dispensing system for dispensing eye drops upon an eye which: can be easily used by patients having poor vision and/or hand control; is simple and economical to manufacture and use; prevents the eye drop bottle from contacting the eye and/or eyelid; prevents improper pressure being applied to the upper eyelid and/or eye; and promotes the instillation of the correct number of eye drops.

SUMMARY OF THE INVENTION

In accordance with the invention, the foregoing advantages have been achieved through the present eye drop dispensing system for dispensing eye drops upon an eye of an eye drop user. The present invention includes: a reservoir adapted to store the eye drop solution; a nozzle associated with the reservoir in fluid communication therewith; and a support structure adapted to support the nozzle and reservoir above the eye in a spaced relation therefrom, the support structure including a truncated, substantially cone-shaped member having upper and lower ends and a sloping wall surface therebetween; the upper end including means for releasably securing the reservoir and nozzle to the truncated cone-shaped member; the lower end adapted to be disposed on a bony structure surrounding the eye; the sloping wall surface extending between the upper and lower ends including a single opening therein which is adapted to permit a finger of the eye drop user to be inserted therethrough to retract the lower eyelid open and to maintain the lower eyelid in its open position while an eye drop is being dispensed and to overcome the eye drop user's eyelid-blink reflex.

A feature of the present invention resides in the fact that the sloping wall surface of the support structure at the lower end thereof may be disposed in a plane which is substantially parallel to the upper end of the support structure. Another feature of the present invention is that the opening formed in the sloping wall surface may extend from a location approximately intermediate the upper and lower ends of the support structure, to and through the lower end of the support structure.

In accordance with the invention, the foregoing advantages have also been achieved through the present eye drop bottle support for spacing the eye drop bottle from an eye drop user's eye and for positioning the eye drop bottle above the eye. The present invention includes: a substantially truncated cone-shaped member having upper and lower ends, and a sloping wall surface therebetween; the upper end including means for releasably securing the eye drop bottle to the truncated cone-shaped member; the lower end of the truncated cone-shaped member being adapted to be disposed on a bony structure surrounding the eye; and the sloping wall surface extending between the upper and lower ends having a single opening therein which is adapted to permit a finger of the eye drop user to be inserted therethrough to retract the lower eyelid open and to maintain the lower eyelid in its open position while an eye drop is dispensed from the eye drop bottle.

Another feature of the present invention is that the sloping wall surface of the cone-shaped member may be translucent or transparent and the upper end of the cone-shaped member may be opaque. A further feature of the present invention is that a portion of the lower end of the cone-shaped member may include an outwardly extending flange member, the flange member being disposed opposite the opening formed in the sloping wall surface, the flange member being adapted to have indicia thereon.

The eye drop dispensing system and eye drop bottle support of the present invention, when compared with previously proposed prior art eye drop dispensers and attachments therefor, have the advantages of: being simple and economical to manufacture and use; being easily used by patients having poor vision and/or hand control; preventing bacterial contamination of the liquid medication from contact with the patient's eye and/or eyelid; preventing improper pressure to the upper eyelid and/or eye; and promoting the instillation of the correct number of eye drops upon the eye.

BRIEF DESCRIPTION OF THE DRAWINGS

In the drawing:

FIG. 1 is a perspective view of an eye drop dispensing system in accordance with the present invention;

FIG. 2 is a cross-sectional view of an eye drop bottle support taken along line 2—2 of FIG. 1, in accordance with the present invention; and FIG. 3 is a perspective view illustrating the use of an eye drop dispensing system in accordance with the present invention.

The invention will be described in connection with the preferred embodiment, and it will be understood that it is not intended to limit the invention to that embodiment. On the contrary, it is intended to cover all alternatives, modifications, and equivalents as may be included within the spirit and scope of the invention and defined by the appended claims.

DETAILED DESCRIPTION OF THE INVENTION

In FIG. 1, an eye drop dispensing system 40 in accordance with the present invention is shown to generally comprise: a reservoir, or eye drop bottle, 41 adapted to store the eye drop solution, 42; a nozzle 43 associated with the reservoir 41 in fluid communication therewith; and a support structure, or eye drop bottle support, 45, to be hereinafter described in greater detail. Eye drop bottle, or reservoir, 41 may be of conventional design as is common in the art for liquid solutions of medications or cleansing fluids for the eye. Bottle 41 is typically manufactured of a convention, flexible plastic material, whereby upon squeezing of the bottle 41 results in drops 46 (FIG. 3) of the eye drop solution 42 being dispensed through nozzle 43. Nozzle 43 may also be of conventional construction and made of a suitable plastic material, and is typically threadedly received upon eye drop bottle 41.

With reference now to FIGS. 1 and 2, the support structure, or eye drop bottle support, 45 includes a truncated, substantially cone-shaped member 47 having upper and lower ends 48, 49 and a sloping wall surface 50 therebetween. The upper end 48 preferably includes a means for releasably securing 51 the reservoir, or eye drop bottle, 41 and nozzle 43 to the truncated cone-shaped member 47. Preferably, the releasable securing means 51 comprises a tapered opening 52 disposed in the upper end 48 of cone-shaped member 47; opening 52 being tapered to cooperate with the plastic nozzle 43 of eye-drop bottle 41. Thus, nozzle 43 can be press-fitted within opening 52, whereby it is frictionally engaged by the wall surface 53 which forms opening 52 in the upper end 48 of the truncated cone-shaped member 47. Releasable securing means 51 thus permits support structure 45 to be used with a wide variety of different shaped eye drop bottles, or reservoirs, 41. It should of course be readily apparent to one of ordinary skill in the art that any other suitable, releaseable securing means could be utilized to secure nozzle 43 and eye-drop bottle 41 to the support structure 45, such as by threads formed in the upper end 48 of cone-shaped member 47, which threads (not shown) could cooperate with mating threads formed upon nozzle 43.

The sloping wall surface 50 of the cone-shaped member 47 which extends between the upper and lower ends 48, 49 preferably includes a single opening 54 therein, which as will be hereinafter described in greater detail, is adapted to permit a finger 55 of an eye-drop user, or patient, 56 to be inserted through opening 54 to retract the patient's lower eyelid 57 open and to maintain the lower eyelid 57 in its open position while an eye drop 46 is being dispensed into eye 58 as seen in FIG. 3.

Support structure, or eye-drop bottle support, 45 is preferably manufactured from a suitable, plastic material having the requisite strength characteristics. Examples are any number of conventional plastic materials, such as polystyrene or polyethelene. The lower end 49 of cone-shaped member 47 can be provided with a smooth, slightly rounded surface, so that the cone-shaped member 47 will not scratch or injure the patient 56. Use of a plastic material will also permit the insertion of nozzle 43 into releasable securing means 51, as previously described.

Preferably, as seen in FIG. 2, the sloping wall surface 50 of the support structure 45 at the lower end 49 thereof is disposed in a plane which is substantially parallel to the upper end 48 of the support structure, or eye-drop bottle support, 45. As will be hereinafter described in greater detail in connection with FIG. 3, the foregoing described construction permits the eye-drop bottle 41 to be adequately supported upon the patient 56, as will be hereinafter described in greater detail. Also as seen in FIGS. 1 and 2, the opening 54 formed in the sloping wall surface 50 preferably extends from a location approximately intermediate the upper and lower ends 48, 49 of the support structure 45, to and through the lower end 49 of the support structure, or eye drop bottle support, 45. Further, the sloping wall surface 50 of the truncated, cone-shaped member 47 is either translucent or transparent, and the upper end 48 is opaque. The foregoing light transmitting relationships can be accomplished by conventional surface treatments of the wall surface 50 or upper end 48, during the conventional molding process whereby cone-shaped member 47 is manufactured; or alternatively, the upper end 48 can be made opaque as by painting or covering with an opaque material. Having an opaque upper end 48 assists the patient 56 in focusing his or her eye upon opening 52 and the nozzle 43 therein, in order to assist the patient in proper eye drop 46 instillation, as will be hereinafter described in greater detail.

As seen in FIGS. 1 and 2 a portion of the lower end 49 of the support structure, or eye-drop bottle support, 45 may include an outwardly extending flange member 60, which flange member is disposed opposite the opening 54 in the sloping wall surface 50. Flange member 60 is preferably disposed in a plane which is substantially parallel to and coplanar with a plane in which the lower end 49 of the sloping wall surface 50 is disposed. Flange member 60 may have suitable printed indicia, such as "PLACED UPON EYEBROW", disposed thereon, and as will be hereinafter described in greater detail is adapted to provide additional support for the support structure, or eye-drop bottle support, 45 upon the patient 56.

With reference now to FIG. 3, the use of the eye-drop dispensing system 40 of the present invention will be described in greater detail. After eye-drop bottle 41, with nozzle 43 thereon, has been inserted into releaseable securing means 51, patient 56 would either lie down or sit in a chair while grasping the eye-drop bottle 41 and support structure 45 in one of his or her hands. The support structure 45 would be placed over the patient's eye 58 so that the patient would be looking upwardly toward nozzle 43 surrounded by the opaque upper end 48 of the cone-shaped member 47. Flange member 60 would rest upon the patient's eyebrow 61, under which is the bony structure which is a part of the patient's skull which surrounds eye 58. Patient 56 would then insert his or her finger 55 through opening 54 until finger 56 touches the skin near the lower eyelid 57 and then gently pull the skin downwardly in order to retract the lower eyelid 57 into its open position. The patient 56 would not be directly pressing against the eye 58, although the patient 56 could press hard on his or her cheekbone which is disposed beneath finger 55. Finger 55 thus serves to keep the lower eyelid 57 open so that upon squeezing eye-drop bottle 41 with his or her other hand, an eye drop 46 will fall upon eye 58.

It should be noted that the eye drop bottle 41 could alternatively be releaseably secured to truncated, cone-shaped member 47 after cone-shaped member 47, or support structure 45 has been placed upon the patient, in the manner previously described. It should be noted that use of the support structure, or eye-drop bottle support, 45 in the manner previously described, permits patient 56 to overcome the eyelid-blink reflex, which may be voluntary or involuntary, during eye drop instillation, in that finger 55 firmly, but safely, keeps lower eyelid 57 in its open position. The use of only one opening 54 in conjunction with the indicia appearing upon flange member 60, serves to insure that patient 56 will not improperly apply any pressure upon the eye 58, which can occur if the upper eyelid 60 is pulled upon. Opening 54 thus serves to insure that only the lower eyelid 57 is retracted and opened. Insofar as the nozzle 43 is sufficiently spaced from eye 58, there can be no contamination of nozzle 43 or the liquid medication 42 contained within eye drop bottle 41, nor can nozzle 43 inadvertently strike and damage eye 58. The translucency or transparency of the sloping wall surface 50 permits another individual (not shown) to safely instill eye drops in the eye 58 of patient 56, when patient 56 does not have the minimal eye-hand control necessary to use dispensing system 40. The other individual may thus be able to easily use dispensing system 40 and to readily keep the patients lower eyelid 57 open while maintaining a proper spacing of the nozzle 43 from eye 58.

It is to be understood that the invention is not limited to the exact details of construction, operation, exact materials, or embodiment shown and described, as obvious modifications and equivalents will be apparent to one skilled in the art; for example, the support structure could be cylindrical, rather than cone-shaped. Accordingly, the invention is therefore to be limited only by the scope of the appended claims.

What is claimed is:

1. An eye drop dispensing system for dispensing eye drops upon an eye drop user, comprising:
    a reservoir adapted to store the eye drop solution;
    a nozzle associated with the reservoir in fluid communication therewith; and
    a support structure adapted to support the nozzle and reservoir above the eye in a spaced relation therefrom, the support structure including a truncated, substantially cone-shaped member having upper and lower ends and a sloping wall surface therebetween; the upper end including means for releasably securing the reservoir and nozzle to the truncated cone-shaped member; the lower end adapted to be disposed on a bony structure surrounding the eye; the sloping wall surface extending between the upper and lower ends including a single opening therein, the opening extending from a location approximately intermediate the upper and lower ends of the support structure to and through the lower end of the support structure, the opening being adapted to permit a finger of the eye drop user to be inserted therethrough to retract the lower eyelid open and to maintain the lower eyelid in its open position while an eye drop is being dispensed and to overcome the eye drop user's eyelid-blink reflex.

2. The dispensing system of claim 1, wherein the sloping wall surface of the support structure at the lower end thereof is disposed in a plane which is substantially parallel to the upper end of the support structure.

3. The dispensing system of claim 1, wherein a portion of the lower end of the support structure includes an outwardly extending flange member, the flange member being disposed opposite the opening formed in the sloping wall surface, the flange member being adapted to have indicia thereon.

4. The dispensing system of claim 3, wherein the flange member is disposed in a plane which is substantially parallel to a plane in which the lower end of the sloping wall surface is disposed, and the flange member is further adapted to provide additional support for the support structure upon the bony structure surrounding the eye.

5. The dispensing system of claim 1, wherein the sloping wall surface of the support structure is translucent or transparent and the upper end of the support structure is opaque.

6. An eye drop bottle support for spacing the eye drop bottle from an eye drop user's eye and for positioning the eye drop bottle above the eye, comprising:
   a truncated, substantially cone-shaped member having upper and lower ends, and a sloping wall surface therebetween;
   the upper end including means for releasably securing the eye drop bottle to the truncated cone-shaped member;
   the lower end of the truncated cone-shaped member being adapted to be disposed on a bony structure surrounding the eye; and
   the sloping wall surface extending between the upper and lower ends having a single opening therein extending from a location approximately intermediate the upper and lower ends of the cone-shaped member to and through the lower end of the cone-shaped member, the opening being adapted to permit a finger of the eye drop user to be inserted therethrough to retract the lower eyelid open and to maintain the lower eyelid in its open position while an eye drop is dispensed from the eye drop bottle and to overcome the eye drop user's eyelid-blink reflex.

7. The eye drop bottle support of claim 6, wherein the sloping wall surface of the cone-shaped member at the lower end thereof is disposed in a plane which is substantially parallel to the upper end of the cone-shaped member.

8. The eye drop bottle support of claim 6, wherein a portion of the lower end of the cone-shaped member includes an outwardly extending flange member, the flange member being disposed opposite the opening formed in the sloping wall surface, the flange member being adapted to have indicia thereon.

9. The eye drop bottle support of claim 8, wherein the flange member is disposed in a plane which is substantially parallel to a plane in which the lower end of the sloping wall surface is disposed, and the flange member is further adapted to provide additional support for the cone-shaped member upon the bony structure surrounding the eye.

10. The eye drop bottle support of claim 6, wherein the sloping wall surface of the cone-shaped member is translucent or transparent and the upper end of the cone-shaped member is opaque.

* * * * *